US 6,405,729 B1

(12) United States Patent
Thornton

(10) Patent No.: US 6,405,729 B1
(45) Date of Patent: Jun. 18, 2002

(54) ORAL APPLIANCE FOR IMPROVING BREATHING AND METHOD OF CONSTRUCTING SAME

(76) Inventor: W. Keith Thornton, 5524 Edlen, Dallas, TX (US) 75220

( * ) Notice: Subject to any disclaimer, the term of this patent is extended or adjusted under 35 U.S.C. 154(b) by 0 days.

(21) Appl. No.: 09/543,405

(22) Filed: Apr. 5, 2000

(51) Int. Cl.$^7$ .................................................. A61F 5/56
(52) U.S. Cl. .................. 128/848; 128/206.29; 128/859; 128/861; 433/6; 433/7; 433/18; 433/19; 433/36; 602/902
(58) Field of Search ................................. 128/848, 859, 128/861, 206.29; 433/6, 7, 18, 19, 36, 37; 602/902

(56) References Cited

U.S. PATENT DOCUMENTS

| | | | |
|---|---|---|---|
| 690,663 A | 1/1902 | Pratt | |
| 746,869 A | 12/1903 | Moulton | |
| 774,446 A | 11/1904 | Moulton | |
| 885,196 A | 4/1908 | Steil | |
| 893,213 A | 7/1908 | Whiteway | |
| 1,076,534 A | 10/1913 | Wallen | |
| 1,146,264 A | 7/1915 | Kelly | |
| 1,483,694 A | 2/1924 | Stukey | |
| 1,649,664 A | 11/1927 | Carter | |
| 1,674,336 A | 6/1928 | King | |
| 2,171,695 A | 9/1939 | Harper | 32/19 |
| 2,178,128 A | 10/1939 | Waite | 128/136 |
| 2,383,649 A | 8/1945 | Heidbrink | 128/142 |
| 2,424,533 A | 7/1947 | Faires | 128/136 |
| 2,505,028 A | 4/1950 | Boeger | 128/215 |
| 2,521,039 A | 9/1950 | Carpenter | 128/136 |
| 2,521,084 A | 9/1950 | Oberto | 128/141 |
| 2,531,222 A | 11/1950 | Kesling | 32/14 |

(List continued on next page.)

FOREIGN PATENT DOCUMENTS

| | | | |
|---|---|---|---|
| AU | 78762/94 | 4/1995 | ............. A61F/5/56 |
| AU | 27647/95 | 1/1996 | ........... A62B/18/98 |
| DE | 156627 | 12/1904 | |
| EP | 0312368 | 4/1989 | ............. A61F/5/56 |
| EP | 0359135 | 3/1990 | ........... A63B/71/10 |
| GB | 1569129 | 6/1980 | ............. A61F/5/56 |
| WO | WO 91/2777 | 9/1991 | ............. A61C/9/00 |
| WO | WO 98/20924 | 5/1998 | .......... A61M/15/08 |

OTHER PUBLICATIONS

Mayo Clinic Health Letter, vol. 13, No. 7, "Snoring.", Jul. 1995.

Photocopies of 2–piece dental device manufactured by Currie–Gibson Dental Laboratory, Inc. prior to Apr. 13, 1993.

Farrar & McCarty, "A Clinical Outline of Temporomandibular Joint Diagnosis and Treatment," Normandie Study Group for TMJ Dysfunction, 3 pages, 1983.

(List continued on next page.)

Primary Examiner—John G. Weiss
Assistant Examiner—Darwin Erezo
(74) Attorney, Agent, or Firm—Baker Botts L.L.P.

(57) ABSTRACT

A device (10) for improving a user's breathing includes an upper arch (12) that is adapted to receive at least some of the user's upper teeth and a lower arch (14) that is adapted to receive at least some of the user's lower teeth. A deformable material (16) couples the upper arch (12) to the lower arch (14) and includes an aliphatic polyester. The deformable material (16) is bonded to the upper arch (12) and bonded to the lower arch (14) to fix the forward position of the lower arch (14). The aliphatic polyester may include a polycaprolactone polymer. The deformable material (16) may be placed in a deformable state to allow the lower arch (14) to be adjusted to a new position.

20 Claims, 4 Drawing Sheets

U.S. PATENT DOCUMENTS

| | | | |
|---|---|---|---|
| 2,574,623 A | 11/1951 | Clyde | 128/136 |
| 2,590,118 A | 3/1952 | Oddo, Jr. | 128/136 |
| 2,627,268 A | 2/1953 | Leppich | 128/136 |
| 2,833,278 A | 5/1958 | Ross | 128/136 |
| 2,867,212 A | 1/1959 | Nunn, Jr. | 128/136 |
| 2,882,893 A | 4/1959 | Godfroy | 128/136 |
| 3,037,501 A | 6/1962 | Miller | 128/141 |
| 3,064,354 A | 11/1962 | Pos | 32/19 |
| 3,107,668 A | 10/1963 | Thompson | 128/136 |
| 3,124,129 A | 3/1964 | Grossberg | 128/136 |
| 3,132,647 A | 5/1964 | Corniello | 128/136 |
| 3,219,033 A | 11/1965 | Wallshein | 128/136 |
| 3,277,892 A | 10/1966 | Tepper | 128/172.1 |
| 3,312,216 A | 4/1967 | Wallshein | 128/136 |
| 3,321,832 A | 5/1967 | Weisberg | 32/32 |
| 3,434,470 A | 3/1969 | Strickland | 128/136 |
| 3,457,916 A | 7/1969 | Wolicki | 128/136 |
| 3,513,838 A | 5/1970 | Foderick et al. | 128/136 |
| 3,522,805 A | 8/1970 | Wallshein | 128/136 |
| 3,658,058 A | 4/1972 | Neidhart et al. | 128/147 |
| 3,690,004 A | 9/1972 | Frush | 32/17 |
| 3,854,208 A | 12/1974 | Arant | 32/19 |
| 3,864,832 A | 2/1975 | Carlson | 128/136 |
| 3,871,370 A | 3/1975 | McDonald | 128/136 |
| 3,882,601 A | 5/1975 | Jahn | 32/17 |
| 3,884,226 A | 5/1975 | Tepper | 128/136 |
| 4,016,650 A | 4/1977 | Leusner et al. | 32/17 |
| 4,026,024 A | 5/1977 | Tradowsky | 32/19 |
| 4,114,614 A | 9/1978 | Kesling | 128/136 |
| 4,169,473 A | 10/1979 | Samuelson | 128/136 |
| 4,182,312 A | 1/1980 | Mushabac | 433/68 |
| 4,227,877 A | 10/1980 | Tureaud et al. | 433/37 |
| 4,233,972 A | 11/1980 | Hauff et al. | 128/205 |
| 4,289,127 A | 9/1981 | Nelson | 128/207.14 |
| 4,304,227 A | 12/1981 | Samelson | 128/136 |
| 4,345,592 A | 8/1982 | Giorgini et al. | 128/204 |
| 4,345,593 A | 8/1982 | Sullivan | 128/204 |
| 4,376,628 A | 3/1983 | Aardse | 433/80 |
| 4,382,783 A | 5/1983 | Rosenberg | 433/19 |
| 4,392,490 A | 7/1983 | Mattingly et al. | 128/202 |
| 4,433,956 A | 2/1984 | Witzig | 433/7 |
| 4,439,147 A | 3/1984 | Magill et al. | 433/3 |
| 4,439,149 A | 3/1984 | Devincenzo | 433/6 |
| 4,470,413 A | 9/1984 | Warncke | 128/201.18 |
| 4,495,945 A | 1/1985 | Liegner | 128/200.26 |
| 4,505,672 A | 3/1985 | Kurz | 433/6 |
| 4,530,662 A | 7/1985 | Andersson et al. | 433/37 |
| 4,553,549 A | 11/1985 | Pope et al. | 128/421 |
| 4,568,280 A | 2/1986 | Ahlin | 433/6 |
| 4,569,342 A | 2/1986 | von Nostitz | 128/136 |
| 4,593,686 A | 6/1986 | Lloyd et al. | 128/136 |
| 4,602,905 A | 7/1986 | O'Keefe, III | 433/41 |
| 4,639,220 A | 1/1987 | Nara et al. | 433/69 |
| 4,655,213 A | 4/1987 | Rapoport et al. | 128/205.25 |
| 4,668,188 A | 5/1987 | Wolfenson et al. | 433/37 |
| 4,669,459 A | 6/1987 | Spiewak et al. | 128/136 |
| 4,676,240 A | 6/1987 | Gardy | 128/207.14 |
| 4,706,683 A | 11/1987 | Chifton et al. | 128/654 |
| 4,715,368 A | 12/1987 | George | 128/136 |
| 4,773,853 A | 9/1988 | Kussick | 433/6 |
| 4,784,123 A | 11/1988 | Robeson | 128/90 |
| 4,799,500 A | 1/1989 | Newbury | 128/859 |
| 4,858,606 A | 8/1989 | Hamlin | 128/204 |
| 4,862,903 A | 9/1989 | Campbell | 128/861 |
| 4,870,962 A | 10/1989 | Sitnik | 128/205 |
| 4,886,056 A | 12/1989 | Simpson | 128/201 |
| 4,892,478 A | 1/1990 | Tateosian et al. | 433/6 |
| 4,901,737 A | 2/1990 | Toone | 128/848 |
| 4,906,234 A | 3/1990 | Voychehovski | 604/79 |
| 4,919,128 A | 4/1990 | Kopala et al. | 128/207.18 |
| 4,932,867 A | 6/1990 | Ueno | 433/69 |
| 4,955,393 A | 9/1990 | Adell | 128/859 |
| RE33,442 E | 11/1990 | George | 128/860 |
| 5,003,994 A | 4/1991 | Cook | 128/848 |
| 5,011,407 A | 4/1991 | Pelerin | 433/48 |
| 5,018,533 A | 5/1991 | Hawkins | 128/848 |
| 5,026,278 A | 6/1991 | Oxman et al. | 433/41 |
| 5,028,232 A | 7/1991 | Snow | 433/24 |
| 5,040,976 A | 8/1991 | Ubel, III et al. | 433/41 |
| 5,042,478 A | 8/1991 | Kopala et al. | 128/207.18 |
| 5,042,506 A | 8/1991 | Liberati | 128/848 |
| 5,046,512 A | 9/1991 | Murchie | 128/848 |
| 5,052,409 A | 10/1991 | Tepper | 128/859 |
| 5,055,039 A | 10/1991 | Abbatte et al. | 433/24 |
| 5,056,534 A | 10/1991 | Wright | 128/848 |
| 5,064,371 A | 11/1991 | Smeltzer | 433/37 |
| 5,065,756 A | 11/1991 | Rapoport | 128/204 |
| 5,066,231 A | 11/1991 | Oxman et al. | 433/214 |
| 5,078,600 A | 1/1992 | Austin | 433/73 |
| 5,092,346 A | 3/1992 | Hays et al. | 128/848 |
| 5,103,838 A | 4/1992 | Yousif | 128/859 |
| 5,112,225 A | 5/1992 | Diesso | 433/48 |
| 5,117,816 A | 6/1992 | Shapiro et al. | 128/200.24 |
| 5,154,184 A | 10/1992 | Alvarez | 128/848 |
| 5,154,609 A | 10/1992 | George | 433/68 |
| 5,183,057 A | 2/1993 | Syrop et al. | 128/845 |
| 5,188,529 A | 2/1993 | Lüth | 433/68 |
| 5,190,457 A | 3/1993 | Schreinemakers | 433/214 |
| 5,193,532 A | 3/1993 | Moa et al. | 128/204 |
| 5,213,498 A | 5/1993 | Pelerin | 433/37 |
| 5,243,971 A | 9/1993 | Sullivan et al. | 128/205 |
| 5,245,995 A | 9/1993 | Sullivan et al. | 128/204 |
| 5,267,862 A | 12/1993 | Parker | 433/215 |
| 5,277,202 A | 1/1994 | Hays | 128/848 |
| 5,284,161 A | 2/1994 | Karell | 128/848 |
| 5,313,960 A | 5/1994 | Tomasi | 128/848 |
| 5,316,020 A | 5/1994 | Truffer | 128/848 |
| 5,320,533 A | 6/1994 | Lee | 433/218 |
| 5,365,945 A | 11/1994 | Halstrom | 128/848 |
| 5,370,533 A | 12/1994 | Bushnell | 433/36 |
| 5,373,859 A | 12/1994 | Forney | 128/846 |
| 5,409,017 A | 4/1995 | Lowe | 128/848 |
| 5,415,544 A | 5/1995 | Oxman et al. | 433/48 |
| 5,427,117 A | 6/1995 | Thornton | 128/848 |
| 5,456,264 A | 10/1995 | Series et al. | 128/725 |
| 5,458,137 A | 10/1995 | Axe et al. | 128/204 |
| 5,477,850 A | 12/1995 | Zegler et al. | 128/202 |
| 5,503,146 A | 4/1996 | Froehlich et al. | 128/204 |
| 5,503,552 A | 4/1996 | Diesso | 433/37 |
| 5,517,983 A | 5/1996 | Deighan et al. | 128/204 |
| 5,537,994 A | 7/1996 | Thornton | 128/205 |
| 5,537,999 A | 7/1996 | Dearman et al. | 128/205 |
| 5,538,000 A | 7/1996 | Rudolph | 128/205 |
| 5,551,419 A | 9/1996 | Froehlich et al. | 128/204 |
| 5,551,872 A | 9/1996 | Mena | 433/37 |
| 5,558,090 A | 9/1996 | James | 128/207.18 |
| RE35,339 E | 10/1996 | Rapoport | 128/204 |
| 5,560,354 A | 10/1996 | Berthon-Jones et al. | 128/205 |
| 5,562,449 A | 10/1996 | Jacobs et al. | 433/215 |
| 5,566,683 A | 10/1996 | Thornton | 128/848 |
| 5,570,704 A * | 11/1996 | Buzzard et al. | 128/848 |
| 5,582,517 A | 12/1996 | Adell | 433/6 |
| 5,592,935 A | 1/1997 | Elstran et al. | 128/205 |
| 5,611,485 A | 3/1997 | Davis | 239/8 |
| 5,642,737 A * | 7/1997 | Parks | 128/848 |
| 5,657,751 A | 8/1997 | Karr, Jr. | 128/205 |
| 5,657,752 A | 8/1997 | Landis et al. | 128/207 |
| 5,676,133 A | 10/1997 | Hickle et al. | 128/205 |
| 5,678,567 A | 10/1997 | Thornton et al. | 128/848 |
| 5,687,715 A | 11/1997 | Landis et al. | 128/207.18 |
| 5,713,349 A | 2/1998 | Keaney | 128/204 |

| | | | |
|---|---|---|---|
| 5,718,244 A | 2/1998 | Thorncton | 128/864 |
| 5,718,500 A | 2/1998 | Vinci guerra et al. | 2/431 |
| 5,720,280 A | 2/1998 | Elstran et al. | 128/205 |
| 5,720,302 A | 2/1998 | Belfer | 128/201.26 |
| 5,746,201 A | 5/1998 | Kidd | 128/206 |
| 5,752,510 A | 5/1998 | Goldstein | 128/207 |
| 5,755,219 A | 5/1998 | Thornton | 128/201 |
| 5,807,100 A | 9/1998 | Thornton | 433/48 |
| 5,823,193 A * | 10/1998 | Singer et al. | 128/848 |
| 5,829,441 A | 11/1998 | Kidd et al. | 128/848 |
| 5,846,082 A | 12/1998 | Thornton | 433/215 |
| 5,868,138 A * | 2/1999 | Halstrom | 128/848 |
| 5,887,587 A | 3/1999 | Groenke | 128/207 |
| 5,899,691 A * | 5/1999 | Parker et al. | 128/861 |
| 5,941,247 A * | 8/1999 | Keane | 128/848 |
| 5,947,724 A * | 9/1999 | Frantz et al. | 128/848 |
| 5,954,048 A | 9/1999 | Thornton | 128/201 |
| 5,983,892 A | 11/1999 | Thornton | 128/201 |
| 5,988,166 A | 11/1999 | Hayek | 128/205 |
| 6,012,455 A | 1/2000 | Goldstein | 128/207 |
| 6,109,265 A | 8/2000 | Frantz et al. | 128/848 |

OTHER PUBLICATIONS

George, "Treatment of Snoring and Obstructive Sleep Apnea with a Dental Device," General Dentistry, 5 pages, Jul./Aug. 1993.

Database WOI, Section PQ, Week 9039, Derwent Publications, Ltd., London, GB XP–002116355—Abstract "Surgical Mouth Air Duct.", Dec. 15, 1989.

CPAP/PRO® . . . Introducing a New Comfort Level for CPAP Users!! brochure (2 pages), No date.

PCT International Search Report, PCT/US97/08708, 4 pages.

* cited by examiner

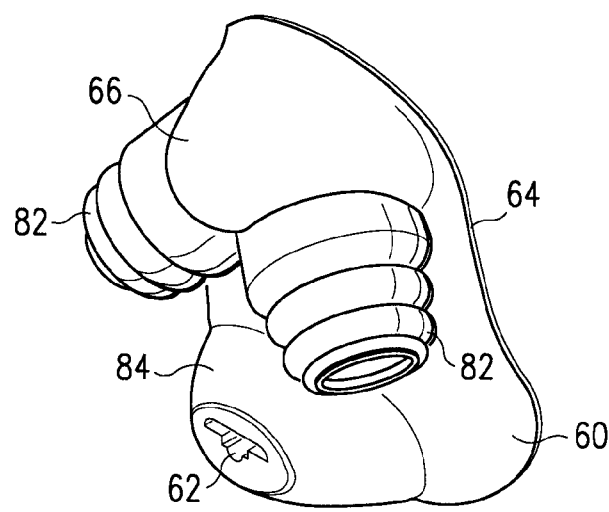
FIG. 5
FIG. 6
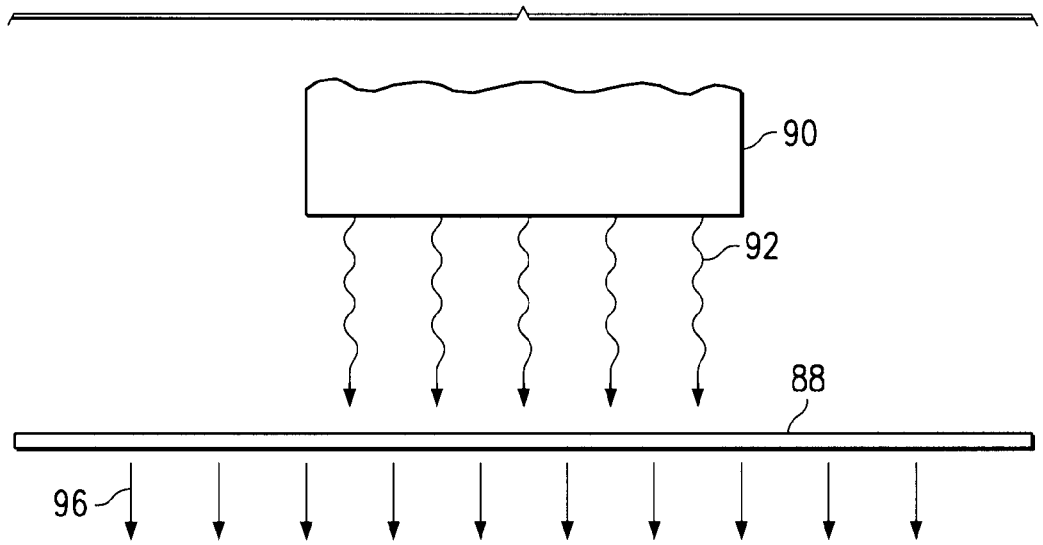
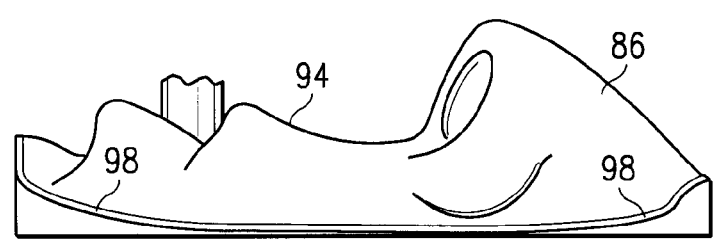

ORAL APPLIANCE FOR IMPROVING BREATHING AND METHOD OF CONSTRUCTING SAME

CROSS REFERENCE TO RELATED APPLICATIONS:

This application is related to U.S. application Ser. No. 09/543,397 entitled "Custom Mask and Method of Forming Same," U.S. application Ser. No. 09/543,398 entitled "Custom Mask Assembly and Method for Making Same," U.S. application Ser. No. 09/543,402 entitled "Device for Improving Breathing and Method of Constructing Same," and U.S. application Ser. No. 09/543,406 entitled "Custom Mask Formed Using an Impression Mask," all filed Apr. 5, 2000 by W. Keith Thornton.

This application is also related to U.S. application Ser. No. 08/594,904, filed Jan. 31, 1996, by W. Keith Thornton and entitled "Device for Improving Breathing," which is a continuation of U.S. application Ser. No. 08/253,949, filed Jun. 3, 1994, by W. Keith Thornton and entitled "Combination Face Mask and Dental Device for Improved Breathing During Sleep" (now U.S. Pat. No. 5,537,994).

This application is also related to U.S. application Ser. No. 08/828,523, filed Mar. 31, 1997, by W. Keith Thornton and entitled "Apparatus for Prevention of Snoring and Improved Breathing During Sleep," which is a file wrapper continuation of U.S. application Ser. No. 08/363,639, filed Dec. 24, 1994, by W. Keith Thornton and entitled "Apparatus for Prevention of Snoring and Improved Breathing During Sleep" (now abandoned), which is a continuation of U.S. application Ser. No. 08/129,598, filed Sept. 29, 1993, by W. Keith Thornton and entitled "Apparatus for Prevention of Snoring and Improved Breathing During Sleep" (now U.S. Pat. No. 5,427,117).

This application is also related to U.S. application Ser. No. 08/787,529, filed Jan. 21, 1997, by W. Keith Thornton and entitled "Method and Apparatus for Adjusting a Dental Device," which is a file wrapper continuation of U.S. application Ser. No. 08/435,277, filed May 5, 1995, by W. Keith Thornton and Andrew O. Jamieson and entitled "Method and Apparatus for Adjusting a Dental Device" (now abandoned), which is a file wrapper continuation of U.S. application Ser. No. 08/218,719, filed Mar. 24, 1994, by W. Keith Thornton and Andrew O. Jamieson and entitled "Method and Apparatus for Adjusting a Dental Device" (now abandoned).

This application is also related to U.S. application Ser. No. 09/333,874, filed Jun. 15, 1999, by W. Keith Thornton and entitled "Device and Method for Improving Breathing and Method for Fitting Same," which is based on U.S. Provisional Application No. 60/089,628, filed Jun. 16, 1998.

This application is also related to U.S. application Ser. No. 09/290,512, filed Apr. 12, 1999, by W. Keith Thornton and entitled "Device for Improving Breathing," which is a continuation of U.S. application Ser. No. 08/878,998, filed Jun. 19, 1997, by W. Keith Thornton and entitled "Device for Improving Breathing" (now U.S. Pat. No. 5,983,892), which is a continuation of U.S. application Ser. No. 08/582, 526, filed Jan. 3, 1996 by W. Keith Thornton and entitled "Device for Improving Breathing" (now abandoned), which is a continuation-in-part of U.S. application Ser. No. 08/253, 949.

This application is also related to U.S. application Ser. No. 09/396,986, filed Sept. 15, 1999 by W. Keith Thornton and entitled "Device for Improving Breathing and Method of Fitting Same."

This application is also related to U.S. application Ser. No. 09/483,741, filed Jan. 17, 2000 by W. Keith Thornton and entitled "Oral Appliance Having a Bonding Layer and Methods for Fitting and Relining Same."

This application is also related to U.S. application Ser. No. 09/554,771, filed May 16, 2000 by W. Keith Thornton and entitled "Device and Method for Improving Breathing."

TECHNICAL FIELD OF THE INVENTION

This invention relates generally to oral appliances and in particular to an oral appliance for improving breathing and a method of constructing the same.

BACKGROUND OF THE INVENTION

Many people experience breathing problems on a recurring basis, which often results in difficulty sleeping, in snoring, or in other more serious conditions such as obstructive sleep apnea. One treatment for such breathing problems involves use of a device inserted into a user's mouth for extending the user's lower jaw forward. These devices help to open the user's breathing passage more fully to allow easier breathing through the user's nose and mouth.

As technology advances and people with breathing problems demand increased performance and comfort, improving the breathing of the users becomes increasingly important. Previous devices for improving breathing include upper and lower arches connected using some mechanical apparatus to move the lower arch forward and thus extend the user's lower jaw forward. Alternatively, some devices have used an acrylic material to connect the upper and lower arches. The acrylic material is coupled to the upper and lower arches while heated deformable state and allowed to cool and harden such that the lower arch is extended forward to a fixed position. Although certain of these devices have been effective in treating breathing problems, they are unable to be adjusted once the acrylic hardens and fixes the relative position of the upper and lower arches. As a result, if the user requires greater forward extension of the lower arch due to ineffectiveness, poor fit, or another problem associated with the device having the current forward extension, an entirely new device must be created. This may often be inconvenient, time-consuming, and expensive. This and other deficiencies have made previous devices inadequate to satisfy the needs of many users.

SUMMARY OF THE INVENTION

The oral appliance of the present invention reduces or eliminates the problems and disadvantages associated with previous devices for improving breathing.

According to one embodiment of the present invention, a device for improving a user's breathing includes an upper arch adapted to receive at least some of the user's upper teeth and a lower arch adapted to receive at least some of the user's lower teeth. A deformable material coupling the upper arch to the lower arch includes an aliphatic polyester. The deformable material is bonded to the upper and lower arches to fix the forward position of the lower arch. In a particular embodiment, the aliphatic polyester may include a polycaprolactone polymer. In still another particular embodiment, the deformable material may be placed in a deformable state to allow the lower arch to be adjusted to a new position.

The oral appliance of the present invention provides many important technical advantages of previous devices for improving breathing. The oral appliance includes a deformable material that includes an aliphatic polyester to couple the upper and lower arches. In a more particular embodiment, the aliphatic polyester includes one or more polycaprolactone polymers. The use of an aliphatic polyester such as polycaprolactone allows the relative positions of the upper and lower arches to be repeatedly adjusted, according to a particular user's needs. In contrast to acrylic materials used in previous devices, the deformable material of the present invention may be reheated after fixing the relative positions of the upper and lower arches to place it once again in a deformable state, the lower arch may be extended to a greater or lesser extent, and the deformable material may be allowed to harden to once again fix the relative positions of the upper and lower arches. The ability to adjust the extension of the lower arch after the oral appliance has been used, without creating an entirely new oral appliance, provides an important technical advantage of the present invention. Other technical advantages are readily apparent to those skilled in the art.

BRIEF DESCRIPTION OF THE DRAWINGS

For a more complete understanding of the present invention and its advantages, reference is now made to the following descriptions taken in conjunction with the accompanying drawings, in which like reference numbers indicate like features and wherein:

FIG. 5 illustrates another exemplary custom mask; and

FIG. 6 illustrates exemplary forming of a custom mask.

DETAILED DESCRIPTION OF THE INVENTION

Figure 1:
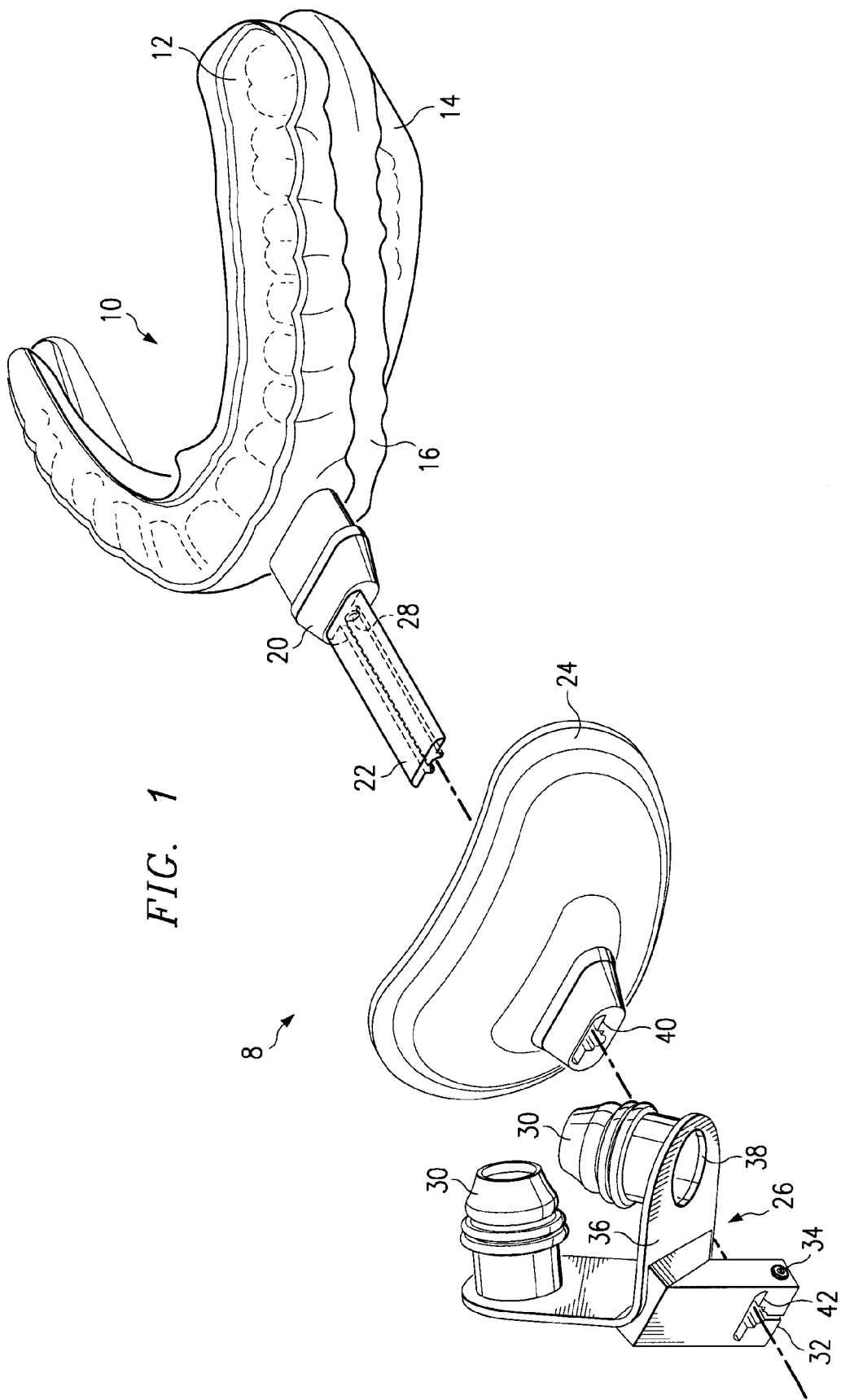
FIG. 1 illustrates a device for improving a user's breathing.
Figure 2A:
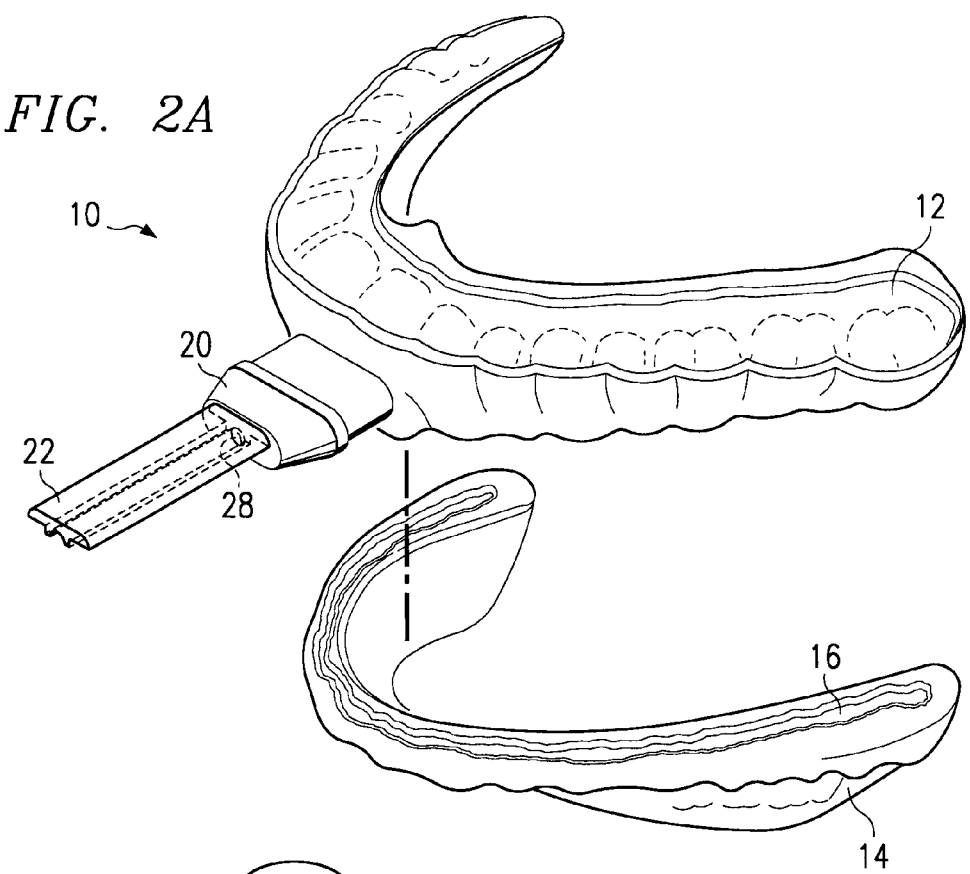
FIGS. 2A and 2B illustrate exemplary coupling of upper and lower arches using a deformable material.

FIG. 1 illustrates a device 8 for improving breathing that includes an oral appliance 10 having an upper arch 12 adapted to receive at least some of a user's upper teeth and a lower arch 14 adapted to receive at least some of the user's lower teeth. Arches 12 and 14 may be any arches suitable for dental or medical uses. For example (and also as shown in FIG. 2A), arches 12 and 14 may be custom arches that have been customized or otherwise formed, using a suitable deformable material, to fit the definition of a particular user. Suitable deformable materials may include, for example only and without limitation, methylmethacrylate, the polycarbonate resin thermoplastic such as that sold as LEXAN, the ethylene-vinyl acetate copolymer resin sold under the name ELVAX, a thermoplastic polymer such as polycaprolactone, or any other suitable deformable material. These materials are known, at least in certain contexts, to those skilled in the art, and other suitable materials may be used without departing from the intended scope of the present invention.

In one embodiment, arches 12 and 14 are heated to temperature appropriate to place the associated deformable material in its deformable state. Arches 12 and 14 are then inserted into the user's mouth, separately or together, and the user bites down to deform deformable material into the shape of at least some of the user's teeth. Arches 12 arch 14 are removed from the user's mouth and allowed to cool and harden. Custom arches 12 and 14 may be formed in this manner by the user or a clinical professional. Arches 12 and 14 may also be formed from conventional dental casts or in any other suitable manner, according to particular needs.

Figure 2B:
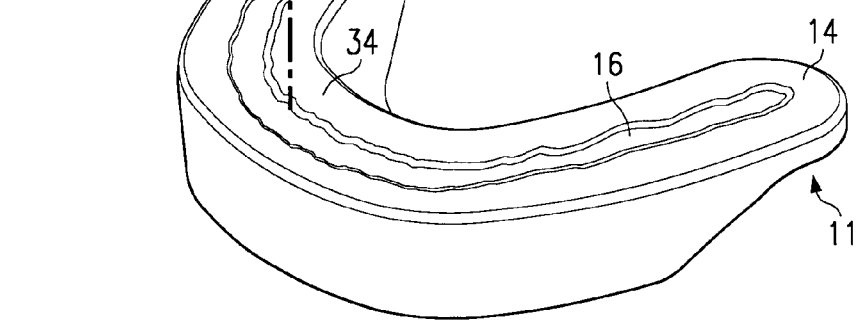

Alternatively, as shown in FIG. 2B, one or both arches 12 and 14 may be non-custom arches that may themselves be adapted to receive a deformable material 18 in which molds of at least some of the user's upper and lower teeth, respectively, may be formed. Deformable material 18 may be the ethylene-vinyl acetate copolymer resin sold under the name ELVAX, a thermoplastic polymer such as polycaprolactone, or another deformable material 18 suitable for forming molds of a user's teeth. In one embodiment, deformable material 18 is heated to approximately 150° F. or another suitable temperature to place deformable material 18 in its deformable state. Arches 12 and 14 are then inserted into the user's mouth, separately or together, and the user bites down to deform deformable material 18 into the shape of at least some of the user's teeth. Arches 12 arch 14 are removed from the user's mouth and allowed to cool and harden. Non-custom arches 12 and 14 may be customized in this manner for a particular user by the user or a clinical professional.

In one embodiment, arch 12 is coupled to arch using a deformable material 16 including one or more of the polycaprolactone polymers or other aliphatic polyesters described in U.S. Pat. Nos. 5,112,225 and 4,784,123, and also in product literature distributed by UNION CARBIDE CORPORATION. One or more polycaprolactone polymers may have the formula:

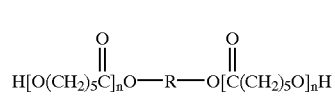

(1)

where R is an aliphatic hydrocarbon and n may range between approximately 300 to approximately 650. However, the present invention contemplates using any suitable polycaprolactone polymer, possibly including a polycaprolactone polymer with another suitable formula.

In a particular embodiment, deformable material 16 includes one or more of the TONE P-700, TONE P-767, or TONE P-787 polycaprolactone polymers manufactured by UNION CARBIDE CORPORATION, singly or in any combination. In a more particular embodiment, deformable material may include approximately thirty parts by volume of TONE P-700 and sixty parts by volume of TONE P-767, together with approximately ten parts by volume of one or more other polymers, depending upon the application and particular needs. A light cured material, another polymer, or any other suitable material, such as a filler, coloring agent, stabilizer, antioxidant, or antimicrobial agent, may be used to replace or combine with a polycaprolactone polymer in forming deformable material 16 having any appropriate characteristics, properties, or uses. The present invention contemplates deformable material 16 including any suitable mixture or other combination of polycaprolactone polymers, other polymers, and other suitable materials, compounds, or compositions.

The TONE set of polycaprolactone polymers are described in U.S. Pat. Nos. 5,112,225 and 4,784,123, and in product literature distributed by UNION CARBIDE CORPORATION, as including homopolymers, block copolymers, graft copolymers, or other polymers containing epsilon-caprolactone. Polymerization may be initiated using a diol, for example and without limitation, ethylene glycol, diethylene glycol, neopentyl glycol, butane diol, hexane diol, or any other appropriate diol. The diol may have the formula:

$$HO—R—OH \quad (2)$$

where R is an aliphatic hydrocarbon.

Deformable material 16 may begin as extruded pellets, beads, or rods of uniform, similar, or differing size, or in other suitable form. Deformable material 16 is heated in a microwave oven, in water or other non-solvent neutral liquid, or in any other suitable manner to between approximately 140° F. and approximately 180° F. to place deformable material 16 in its deformable state. Deformable material 16 may be maintained in this deformable state until the pellets, beads, or rods congeal, coalesce, or otherwise combine to form a deformable mass capable of assuming shape and configuration desired. The deformable material 16 may be placed in a deformable state before, during, or after deformable material 16 is coupled to arches 12 and 14. Deformable material 16 mixes, bonds, reacts, combines, or otherwise couples with the material used to form arches 12 and 14 while deformable material 16 is in a liquid or other deformable state.

In one embodiment, as illustrated in FIGS. 2A and 2B, deformable material 16 is applied to upper arch 12, lower arch 14, or both upper arch 12 and lower arch 14. Arches 12 and 14 are then pressed or otherwise brought together, before or after arches 12 and 14 are inserted into the user's mouth. The user's lower jaw is adjusted forward such that lower arch 14 assumes an appropriate forward position relative to upper arch 12, according to particular needs of the user. Deformable material 16 mixes, bonds, reacts, combines, or otherwise couples to arches 12 and 14 while in a deformable state. Deformable material 16 is allowed to cool and harden to fix the relative positions of arches 12 and 14, the lower arch 14 thereafter being in a fixed forward position relative to upper arch 12. In an alternative embodiment, arches 12 and 14 are inserted into the user's mouth to receive one or more of the user's teeth, and deformable material 16 is delivered to upper arch 12, lower arch 14, or both arches 12 and 14 after arches 12 and 14 have been inserted into the user's mouth. Deformable material 16 may be delivered to arches 12 and 14 while in a liquid, melted, or other deformable state using a syringe, hypodermic needle, hot glue gun, or other delivery device or technique.

Arches 12 and 14 may remain inserted in the user's mouth or may be removed from the user's mouth before, during, or after deformable material 16 fully cools and hardens. Deformable material 16 may be used to couple arches 12 and 14 in the user's home, in the office of a dental, medical, or other clinical professional, or in any other suitable location. Although a particular technique is described, the present invention contemplates any appropriate technique for introducing one or more polycaprolactone polymers between arches 12 and 14 to secure the relative positions of arches 12 and 14, preferably fixing the forward position of lower arch 14 relative to upper arch 12. The relative positions of arches 12 and 14 may be secured to reduce or eliminate breathing problems such as snoring and sleep apnea, or for any other suitable purpose. Also, if adjustment of the position of lower arch 14 becomes necessary or desirable, according to particular needs, the deformable material 16 may be reheated to place deformable material 16 in a deformable state, lower 14 may be adjusted as appropriate, and then deformable material 16 may be allowed to again cool and harden to fix the adjusted position of lower arch 14. Providing adjustability of the lower arch 14 using improved deformable material 16, without requiring a new oral appliance 10 to be constructed, provides an important technical advantage of the present invention over prior devices using acrylic and other materials to couple upper and lower arches.

Referring again to FIG. 1, upper arch 12 includes, supports, or is otherwise coupled to a connecting post 20 having an extended arm 22 for coupling upper arch 12 to a venting seal 24, a nasal flange 26, or any other appropriate component compatible with arm 22, singly or in any appropriate combination. In one embodiment, connecting post 20, arm 22, or both connecting post 20 and arm 22 are removably coupled to the upper arch 12 using a screw or other suitable fastener 28, although connecting post 20 may be fully or partially integral to upper arch 12 without departing from the intended scope of the present invention. As described more fully below, arm 22 may provide standard interface for coupling a variety of accessory or other suitable components to upper arch 12 of oral appliance 10. Moreover, connecting post 20 and arm 22 may be coupled to a variety of oral appliances. For example only and not by way of limitation, connecting post 20 may be coupled to upper arch 12 (whether or not coupled to lower arch 14 using deformable material or otherwise), to an adjustable oral appliance such as that described in U.S. Pat No. 5,954,048, or to any other suitable oral appliance. As a result, using the standard interface that arm 22 provides according to the present invention, a device that incorporates a selected oral appliance and one or more selected accessory components may be constructed to satisfy the user's particular needs, which provides an important technical advantage.

In general, venting seal 24 is shaped to seal around the user's lips to reduce or substantially eliminate venting of air from the user's mouth when device 8 is in use. Venting is known to reduce the effectiveness of continuous positive air pressure (CPAP) treatment or other treatment involving delivery of air or another gas to the user's nose at positive pressure to open the user's breathing passage. When venting occurs, at least some air that would otherwise help force open the breathing passage is lost through the user's mouth. When venting is reduced, more of the air is used to open the breathing passage and the effectiveness of the treatment therefore increases. The venting seal 24 may be formed from any suitable rubberized, vinyl, acrylic, plastic, or other flexible material. Venting seal 24 may be a non-custom item or may be customized to fit the particular user's facial features or any other of the user's particular needs.

Nasal flange 26 is coupled to arm 22 and supports a pair of nasal pillows 30 for delivering air or another gas to the user's nose at positive pressure during the course of CPAP or other suitable treatment. In one embodiment, nasal flange 26 couples to arm 22 using a clamp 32 that may be tightened using screw 34 or any other suitable fastener to secure nasal flange 26 to arm 22. A substantially Y-shaped flange 36 supports the nasal pillows 30 in position to properly seat in the user's nostrils. Another screw or fastener (not explicitly shown) may provide for substantially vertical adjustment of Y-shaped flange 36. Although the present invention contemplates any appropriate nasal pillows 30, nasal pillows 30 are preferably formed from a suitable rubberized, vinyl, acrylic, plastic, or other flexible material such that nasal inserts 34 seat comfortably and adjustably within the user's nostrils while delivering air or other gas at positive pressure from a CPAP system or other external source. Holes 38 in Y-shaped flange 36 receive appropriate hoses or other members (not explicitly shown) to supply nasal pillows 30 with air or other gas for delivery to the user. One or more holes (not explicitly shown) in such hoses or at appropriate places on nasal flange 26 preferably allow exhaled gas, such as carbon dioxide, to escape without reducing the effectiveness of device 10 in delivering air or another gas at a sufficient pressure to force open the user's breathing passage.

Openings 40 and 42 of venting seal 24 and nasal flange 26, respectively, have cross-sections suitable to receive and engage arm 22 of connecting post 20. Moreover, as described above, in one embodiment the cross-section of arm 22 is such that arm 22 provides a standard interface compatible with the openings in a variety of components, including but not limited to venting seal 24 and nasal flange 26. As a result, a system of interchangeable and optional components is provided, all compatible with the common interface of arm 22. Users or their clinical professionals can thus select an appropriate combination of components, according to particular needs. Furthermore, because arm 22 provides a standard interface, different manufacturers may produce components for attachment to arm 22, compatible with that standard interface. The present invention therefore provides important technical advantages over prior devices. Although oral appliance 10 has been described primarily as capable of extending the user's lower jaw forward, the present invention contemplates oral appliance 10 being used primarily to help secure the position of nasal flange 26, or another appropriate mask such as those described more fully below, on the user's face.

In one embodiment, venting seal 24 may be adjusted forward or rearward along arm 22 to position venting seal 24 according to particular needs, providing an important technical advantage. After adjustment, the position of venting seal 24 may be secured using nasal flange 26, a screw or another fastener associated with venting seal 24 (not shown), or in another appropriate manner. For example, when screw 34 is adjusted to tighten clamp 32 and thereby secure the nasal flange 26 to arm 22, the movement of venting seal 24 along arm 22 is limited. Through suitable adjustment and securing of nasal flange 26, venting seal 24, or both nasal flange 26 and venting seal 24 to arm 22, the effectiveness of venting seal 24 may be increased. Prior lip shields for preventing venting have required cumbersome and often intimidating head straps to secure the lip shield to the user's face, along with straps that wrap over the head and under the jaw to hold the user's jaw shut. Despite these measures, prior lip shields were still not able to achieve adequate lip competence in many cases. The present invention overcomes the problems and disadvantages of such techniques.

Figure 3:
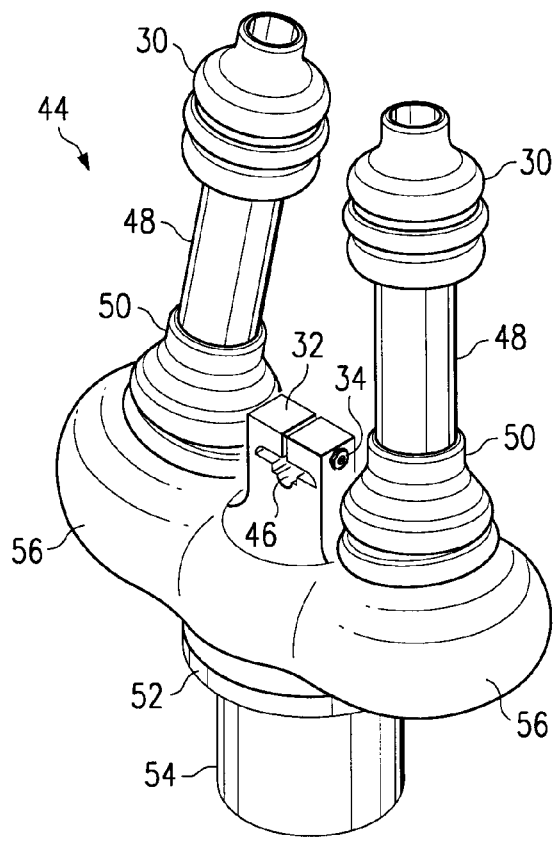
FIG. 3 illustrates an exemplary CPAP interface.

As described above with reference to nasal pillows 30, device 8 may be adapted for use in connection with a CPAP system for supplying air or another gas to the user's nose. Although CPAP systems are primarily discussed, other systems for delivering a breathable gas, such as air, oxygen, or gases used in anaesthesia, at constant or varying pressures, may be used. FIG. 3 illustrates an exemplary CPAP interface 44 that includes an opening 46 having a cross-section suitable to receive arm 22 and thereby couple the interface 44 to upper arch 12 to replace nasal flange 26. A clamp 32 and an associated screw 34 may couple CPAP interface 44 to the arm 22. A pair of tubes 48 couple nasal pillows 30 (described more fully above with reference to FIG. 1) to joints 50 that are coupled to CPAP coupler 52. CPAP coupler 52 may include a tube portion 54 for receiving air or other gas from a CPAP system or other external source. In addition, CPAP coupler 52 may include one or more transition portions 56 to help (possibly in cooperation with joints 50) transition a flow of the air or other gas between tube portion 54 of CPAP coupler 52 and tubes 48. Although the CPAP coupler 52 is described as having a number of portions having possibly different shapes, the present invention contemplates CPAP coupler 52 with any suitable configuration to deliver air or other gas to tubes 48.

In one embodiment, joints 50 may allow substantial adjustment of tubes 48, and therefore nasal pillows 30, to better accommodate the particular user's facial structure. As an example, and without limitation, joints 50 may allow tubes 48 to be placed at the same or different angles relative to the central axes of joints 50 (where the axes for this purpose passes through the openings of joints 50 when joints 50 are in the natural or otherwise undeformed state). In addition, joints 50 may allow tubes 48 to be adjusted either upward (toward the user) or downward (away from the user) in the direction of their length, together with, separate from, or instead of placing tubes 48 at appropriate angles. Using a suitable combination of one or more adjustments of one or both tubes 48, one or both nasal pillows 30 may be optimally positioned to deliver air or other gas to a particular user's nose, providing an important technical advantage. Joints 50 may include any appropriate rubberized, vinyl, acrylic, plastic, or other flexible material to provide such flexibility. One or more holes (not explicitly shown) in hoses 48 or at appropriate places on CPAP interface 44 preferably allow exhaled gas, such as carbon dioxide, to escape without reducing the effectiveness of device 10 in delivering air or another gas at a sufficient pressure to open the user's breathing passage.

Figure 4:
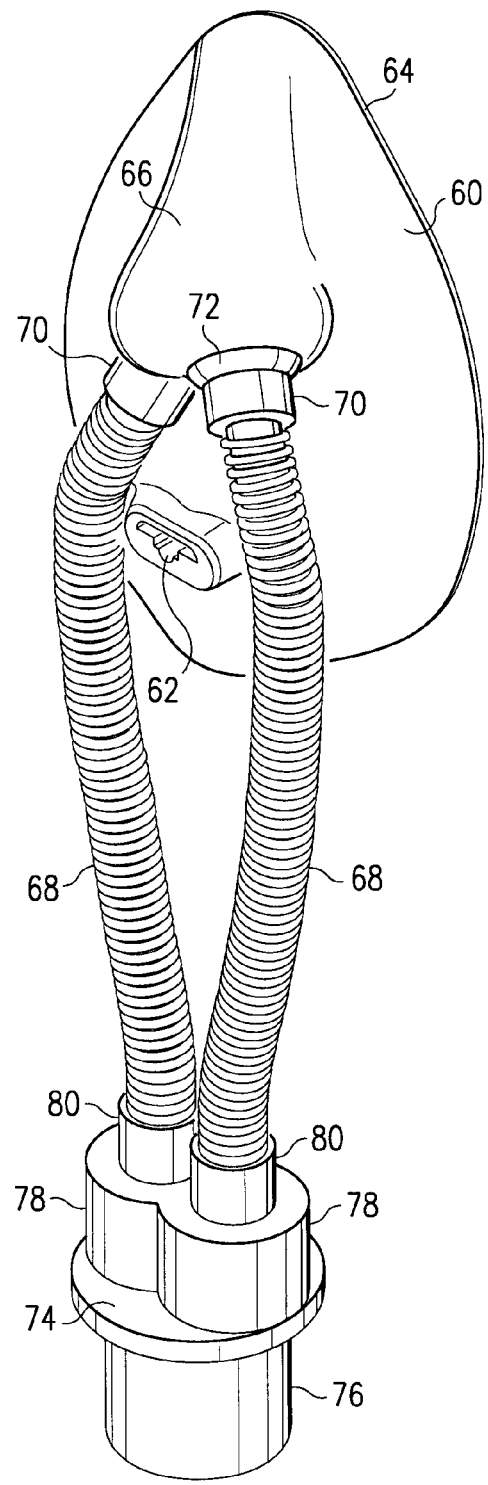
FIG. 4 illustrates an exemplary custom mask.

Referring now to FIG. 4, a custom mask 60 may be used instead of nasal flange 26 or CPAP interface 44. In a particular embodiment, mask 60 includes an opening 62 having a cross-section suitable to receive arm 22, the custom mask 60 being one of perhaps multiple accessory components compatible with the standard interface arm 22 provides. The present invention contemplates custom mask 60 coupling to oral appliance 10 using any suitable connecting post, with or without extended arm 22, as appropriate.

Custom mask 60 is shaped to fit the user's particular facial features to reduce or eliminate venting from around perimeter 64 of mask 60 and, preferably, to increase the user's comfort while wearing mask 60. Mask 60 may include a suitably enlarged nose region 66 adapted to receive the user's nose. One or more hoses 68 for delivering air or other gas to the user's nose include hose couplers 70 for coupling to nose region 66 at seats 72. The hoses 68, hose couplers 70, seats 72, and mask 60 may be integral to or separate from one another, as appropriate. Seat 72 may include one or more screws, clamps, or any other suitable fasteners to fix the associated hose coupler 70 (and thus hose 68) in an effective, comfortable, or otherwise desirable position relative to nose region 66. Hoses 68 may be formed from a rubberized, vinyl, acrylic, plastic, or other flexible material to allow hoses 68 to move to some suitable extent as the user moves without dislodging mask 60 or otherwise decreasing the effectiveness of the device 8. In a particular embodiment, hoses 68 may be conventional "pediatric" tubes.

CPAP coupler 74 couples hoses 68 to a CPAP or other delivery system. The CPAP coupler 74 includes a tube portion 76 for coupling to such a delivery system. Optional transition portions 78 receive hose couplers 80 of hoses 68 and preferably operate to transition a flow of air or other gas between the tube portion 76 and hose couplers 80. Hoses 68, hose couplers 80, transition portions 78, and tube portion 76 may be integral to or separate from one another, as appropriate. In one embodiment, nose region 66, seats 52, hose couplers 50, hoses 48, hose couplers 56, and CPAP coupler 54 cooperate to prevent an undesirable amount of incoming air or another gas, or gases that the user exhales, from venting or otherwise escaping. However, the present invention contemplates mask 60 and associated components allowing a suitable amount of exhaled gases to escape, as appropriate and according to particular needs.

FIG. 5 illustrates an exemplary alternative custom mask 60 that supports a pair of hose couplers 82 coupled to and preferably seated within nose region 66. Hose couplers 82 may be integral to or separate from mask 60, according to particular needs. For substantially optimal fit, hose couplers 82 are preferably formed from a suitable rubberized, vinyl, acrylic, plastic, or other flexible material such that hose couplers 82 may be adjusted for the particular user. Mask 60 may include nasal pillows 30 (not explicitly shown) housed within nose region 66 of mask 60 to deliver air or other gas more directly to the user's nostrils and reduce venting from around the perimeter 64 of mask 60. Mask 60 may include a protruded mouth portion 84 providing space for the user's lips and also possibly for connecting post 20 of oral appliance 10 or a similar component of another associated oral appliance. Mask 60 of FIG. 4 may include a similar mouth portion 84. Like other accessory components described above, mask 60 may include an opening 62 with a cross-section suitable for receiving extended arm 22 of connecting post 20. Although custom masks 60 are primarily described, the present invention contemplates using appropriate non-custom masks 60 to replace one or more of the custom masks 60 described above.

As described above, mask 60 is preferably shaped for the particular-user's facial features to reduce or eliminate venting from the perimeter 64 of mask 60 and to provide increased comfort to the user. In one embodiment, mask 60 is formed using heated polycarbonate techniques that have been applied in other fields, but never with respect to face masks or similar devices. FIG. 6 illustrates exemplary forming of custom mask 60 using one such technique. A alginate "stone" cast or other suitable mold 86 of an appropriate portion of the user's face is constructed using conventional techniques. At a manufacturing facility, a sheet 88 of polycarbonate material having an appropriate size and thickness is heated using a suitable heat source 90, as indicated by arrows 92, placing sheet 88 in a deformable state. Sheet 88 is positioned over mold 86 and pulled or pushed using negative or positive air pressure, respectively, firmly onto surface 94 of mold 86 as indicated by arrows 96. In one embodiment, sheet 88 seals tightly to mold 86 and is deformed to precisely match surface 94 of mold 86. Excess material of sheet 88 may be trimmed as appropriate.

Resulting custom mask 60 typically fits the user much better than any previous custom mask and provides a number of other important technical advantages. Mold 86 may be formed using conventional casting techniques familiar to virtually all practicing dentists. As a result, mold 86 may be created relatively quickly and inexpensively. The heated polycarbonate technique may be carried out in bulk, to form a large number of masks 60, at an existing manufacturing facility already substantially equipped to make other types of items using this technique. The time and cost savings this solution may provide are in addition to a substantially improved fit, reduced venting, and increased comfort relative to previous masks, for which poor fit was often the primary obstacle. In one embodiment, mold 86 may be formed to include a suitable relief border 98 that creates a corresponding ridge or other feature in mask 60. When mask 60 is worn, this ridge presses to some extent into the user's skin to further improve fit, reduce venting, and increase comfort, providing yet another important technical advantage. Although exemplary heated polycarbonate techniques are primarily described, any appropriate heated polycarbonate or other technique may be used to form mask 60.

Although the present invention has been described above in connection with several embodiments, it should be understood that a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A device for improving a user's breathing, comprising:
    an upper arch adapted to receive at least some of the user's upper teeth;
    a lower arch adapted to receive at least some of the user's lower teeth; and
    a deformable material coupling the upper arch to the lower arch, the deformable material comprising an aliphatic polyester bonded to the upper and lower arches to fix the lower arch in a forward position relative to the upper arch.

2. The device of claim 1, wherein the deformable material may be placed in a deformable state to allow the lower arch to be adjusted to a new position.

3. The device of claim 1, wherein the aliphatic polyester comprises a polycaprolactone polymer.

4. The device of claim 1, wherein the aliphatic polyester has the formula:

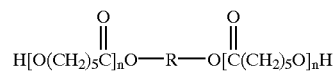

wherein R is an aliphatic hydrocarbon.

5. The device of claim 1, wherein the aliphatic polyester comprises a homopolymer of caprolactone initiated with a diol.

6. The device of claim 1, wherein the deformable material is delivered to at least one arch while the arch is in the user's mouth.

7. The device of claim 1, wherein the deformable material is delivered to the upper and lower arches while the deformable material is in a liquid state.

8. The device of claim 1, wherein the deformable material is chemically bonded to the upper and lower arches.

9. The device of claim 1, wherein the deformable material further comprises a second polymer.

10. The device of claim 1, wherein the upper and lower arches are selected from the group consisting of custom arches and non-custom arches.

11. A device for improving a user's breathing, comprising:
    an upper arch adapted to receive at least some of the user's upper teeth;
    a lower arch adapted to receive at least some of the user's lower teeth; and
    a polycaprolactone polymer material chemically bonded to both the upper and lower arches to secure the lower arch in a fixed forward position relative to the upper arch, the device operable to position the user's lower jaw forward when the device is inserted into the user's mouth to improve the user's breathing, the deformable material operable to be placed in a deformable state to allow the fixed forward position of the lower arch to be adjusted to a new fixed forward position.

12. A method of constructing a device for improving a user's breathing, comprising:
    coupling a deformable material comprising an aliphatic polyester to an upper arch adapted to receive at least some of the user's upper teeth;
    coupling the deformable material to a lower arch adapted to receive at least some of the user's lower teeth; and allowing the deformable to bond to the upper and lower arches to secure the forward position of the lower arch.

13. The method of claim 12, further comprising:

placing the deformable material in a deformable state; and adjusting the lower arch to a new position.

14. The method of claim 12, wherein the aliphatic polyester comprises a polycaprolactone polymer.

15. The method of claim 12, wherein the aliphatic polyester has the formula:

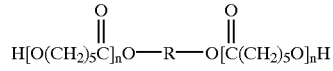

wherein R is an aliphatic hydrocarbon.

16. The method of claim 12, wherein the aliphatic polyester comprises a homopolymer of caprolactone initiated with a diol.

17. The method of claim 12, further comprising delivering the deformable material to at least one arch while the arch is in the user's mouth.

18. The method of claim 12, wherein allowing the deformable material to bond comprises allowing the deformable material to chemically bond to the upper and lower arches.

19. The method of claim 12, wherein the deformable material further comprises a second polymer.

20. The method of claim 12, wherein the upper and lower arches are selected from the group consisting of custom arches and non-custom arches.

* * * * *